United States Patent
He et al.

(10) Patent No.: US 11,130,991 B2
(45) Date of Patent: Sep. 28, 2021

(54) METHOD FOR HIGHLY SENSITIVE DNA METHYLATION ANALYSIS

(71) Applicant: The University of Chicago, Chicago, IL (US)

(72) Inventors: Chuan He, Chicago, IL (US); Boxuan Simen Zhao, Chicago, IL (US); Pradnya Narkhede, Chicago, IL (US); Chang Liu, Chicago, IL (US); Xiaolong Cui, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 16/491,278

(22) PCT Filed: Mar. 8, 2018

(86) PCT No.: PCT/US2018/021591
§ 371 (c)(1),
(2) Date: Sep. 5, 2019

(87) PCT Pub. No.: WO2018/165459
PCT Pub. Date: Sep. 13, 2018

(65) Prior Publication Data
US 2020/0032330 A1    Jan. 30, 2020

Related U.S. Application Data

(60) Provisional application No. 62/468,907, filed on Mar. 8, 2017.

(51) Int. Cl.
*C12Q 1/6844* (2018.01)
*C12Q 1/6806* (2018.01)

(52) U.S. Cl.
CPC ......... *C12Q 1/6844* (2013.01); *C12Q 1/6806* (2013.01)

(58) Field of Classification Search
CPC ............... C12Q 1/6844; C12Q 1/6806; C12Y 201/01037
See application file for complete search history.

(56) References Cited

U.S. PATENT DOCUMENTS

| 6,514,698 B1 * | 2/2003 | Lopez | C12Q 1/6827 435/6.13 |
| 2005/0153296 A1 * | 7/2005 | Berlin | C12Q 2565/518 435/6.12 |

(Continued)

FOREIGN PATENT DOCUMENTS

| WO | WO-2014140309 A1 * | 9/2014 | ............. C12P 19/34 |
| WO | WO 2014/165770 | 10/2014 | |
| WO | WO 2019/126313 | 6/2019 | |

OTHER PUBLICATIONS

Goyal, et al. "Accuracy of DNA Methylation Pattern Preservation by the Dnmt1 Methyltransferase," *Nucleic Acids Research*, 2006, 34(4):1182-1188.

(Continued)

*Primary Examiner* — Joseph G. Dauner
(74) *Attorney, Agent, or Firm* — Norton Rose Fulbright US LLP

(57) ABSTRACT

Methods, compositions and kits are provided to amplify the amount of genomic methylated DNA can by subsequently analyzed and/or sequenced. It has particular use with small amounts of DNA, including, but not limited to cell free DNA samples. In some embodiments, the ratio of polymerase and methyltransferase is controlled in order to provide maximum yields. In some embodiments, a dual primase/polymerase is used.

22 Claims, 7 Drawing Sheets
Specification includes a Sequence Listing.

(56) References Cited

U.S. PATENT DOCUMENTS

| | | |
|---|---|---|
| 2005/0164193 A1* | 7/2005 | Berlin .............. C12Q 2565/627 435/6.12 |
| 2005/0196792 A1 | 9/2005 | Fodor et al. |
| 2005/0202490 A1 | 9/2005 | Makarov et al. |
| 2005/0272070 A1* | 12/2005 | Ehrich ................ C12Q 1/6858 435/6.12 |
| 2006/0223098 A1 | 10/2006 | Lane et al. |
| 2006/0257905 A1 | 11/2006 | Freije et al. |
| 2007/0160991 A1* | 7/2007 | Distler ................ C12Q 1/6886 435/6.12 |
| 2010/0221716 A1* | 9/2010 | Flusberg .............. C12Q 1/6869 435/6.18 |
| 2011/0183320 A1* | 7/2011 | Flusberg .............. C12Q 1/6869 435/6.1 |
| 2011/0301045 A1 | 12/2011 | He et al. |
| 2014/0004511 A1 | 1/2014 | Korlach et al. |
| 2014/0171492 A1* | 6/2014 | Di Ruscio .......... C12N 15/1137 514/44 R |
| 2014/0178881 A1 | 6/2014 | Booth et al. |
| 2014/0322707 A1 | 10/2014 | He et al. |
| 2014/0363815 A1 | 12/2014 | Dahl et al. |
| 2015/0056616 A1 | 2/2015 | He et al. |
| 2015/0266755 A1 | 9/2015 | He et al. |
| 2015/0368694 A1 | 12/2015 | Pan et al. |
| 2016/0040143 A1 | 2/2016 | Picher et al. |
| 2016/0074373 A1 | 3/2016 | He et al. |
| 2016/0115525 A1 | 4/2016 | Ebenstein et al. |
| 2016/0130643 A1* | 5/2016 | Laird-Offringa ...... C12Q 1/686 506/2 |
| 2018/0245128 A1 | 8/2018 | He et al. |
| 2020/0190581 A1 | 6/2020 | He et al. |

OTHER PUBLICATIONS

Guo, et al. "Single-cell methylome landscapes of mouse embryonic stem cells and early embryos analyzed using reduced representation bisulfite sequencing," *Genome Research*, 2013, 23(12):2126-2135.

International Search Report and Written Opinion issued in International Patent Application No. PCT/US2018/021591, dated Jun. 15, 2018.

Lorthongpanich et al. "Single-cell DNA-methylation analysis reveals epigenetic chimerism in preimplantation embryos," *Science*, 2013, 341(6150):1110-1112.

Picher, et al. "TruePrime is a novel method for whole-genome amplification from single cells based on TthPrimPol," *Nature Communications*, 2016, 7:13296.

Smallwood, et al. "Single-cell genome-wide bisulfite sequencing for assessing epigenetic heterogeneity," *Nature Methods*, 2014, 11(8):817-820.

Weber, et al. "Chromosome-wide and promoter-specific analyses identify sites of differential DNA methylation in normal and transformed human cells," *Nature Genetics*, 2005, 37:853-862.

Xue, et al. "Label-Free Molecular Beacon-Based Quadratic Isothermal Exponential Amplification: a Simple and Sensitive One-Pot Method to Detect DNA Methyltransferase Activity," *Chemical Communications*m, 2015, 51(70):13538-13541.

* cited by examiner

*NFATC1* locus: hypermethylated

CCCCTTGCAA CAAGAGGAAG TACAGCCTCA ACGGCCGGCA GCCGCCCTAC TCACCCCACC

ACTCGCCCAC GCCGTCCCCG CACGGCTCCC CGCGGGTCAG CGTGACCGAC GACTCGTGGT

TGGGCAACAC CACCCAGTAC ACCAGCTCGG CCATCGTGGC CGCCATCAAC GCGCTGACCA

CCGACAGCAG CCTGGACCTG GGAGAT   (SEQ ID NO:7)

*MAPK8IP2* locus: unmethylated

GGCTGTGCAG TCTCTACTGA GTGCTCAAAG TCCACTTTTA GCCCCAGCCA GCATCCTCTG AGTACCTTGT

GCTC̊GATTCT GAATCCAGCC CTGCTC̊GGC̊G ACCCTC̊GTGC AGAC̊GTCCC̊C GTGCAGCCC̊C GGTCAGCACC

C̊CGTGGGGAC AGCTC̊CGATC AGCACC̊C̊GAC̊ GGC̊GGACAGC TCTCCC̊GC̊G CCTCC̊CGCCT C̊GCC̊CGCCAC

CC̊CGCTCC̊GG GC̊CGCACC̊CG GGTTAGGGTT CCTGGGGGGA TC   (SEQ ID NO:8)

● 5mCpG     ○ CpG

FIG. 2 a

| gDNA input (ng) | Dnmt1 (unit) | Phi29 (unit) | Hypermethylated locus ||||| Unmethylated locus |||||
|---|---|---|---|---|---|---|---|---|---|---|---|---|
| | | | total 5mCpG sites | 5mCpG sites detected | 'C' reads (%) | 'N' or 'Y' reads (%) | 'T' reads (%) | total CpG sites | CpG sites detected | 'C' reads (%) | 'N' or 'Y' reads (%) | 'T' reads (%) |
| 10 | 30 | 2 | 20 | 19 | 100.0 | 0.0 | 0.0 | 21 | 21 | 0.0 | 0.0 | 100.0 |
| 10 | 20 | 2 | 20 | 18 | 22.2 | 38.9 | 38.9 | 21 | 21 | 0.0 | 0.0 | 100.0 |
| 10 | 20 | 5 | 20 | 17 | 23.5 | 52.9 | 23.5 | 21 | 21 | 0.0 | 0.0 | 100.0 |
| 10 | 0 | 10 | 20 | 18 | 0.0 | 0.0 | 100.0 | 21 | 21 | 0.0 | 0.0 | 100.0 | b

| gDNA input (pg) | Dnmt1 (unit) | Phi29 (unit) | Hypermethylated locus ||||| Unmethylated locus |||||
|---|---|---|---|---|---|---|---|---|---|---|---|---|
| | | | total 5mCpG sites | 5mCpG sites detected | 'C' reads (%) | 'N' or 'Y' reads (%) | 'T' reads (%) | total CpG sites | CpG sites detected | 'C' reads (%) | 'N' or 'Y' reads (%) | 'T' reads (%) |
| 10000 | 30 | 2 | 20 | 19 | 100.0 | 0.0 | 0.0 | 21 | 21 | 0.0 | 0.0 | 100.0 |
| 1000 | 30 | 2 | 20 | 18 | 88.9 | 11.1 | 0.0 | 21 | 21 | 0.0 | 0.0 | 100.0 |
| 500 | 30 | 2 | 20 | 19 | 94.7 | 5.3 | 0.0 | 21 | 21 | 0.0 | 0.0 | 100.0 |
| 100 | 30 | 2 | 20 | 18 | 88.9 | 11.1 | 0.0 | 21 | 21 | 0.0 | 0.0 | 100.0 |
| 50 | 30 | 2 | 20 | 19 | 94.7 | 5.3 | 0.0 | 21 | 21 | 0.0 | 0.0 | 100.0 |
| 10 | 30 | 2 | 20 | 18 | 88.9 | 11.1 | 0.0 | 21 | 21 | 0.0 | 0.0 | 100.0 |
| 5 | 30 | 2 | 20 | 18 | 94.4 | 5.6 | 0.0 | 21 | 21 | 0.0 | 0.0 | 100.0 |

FIG. 4A-B

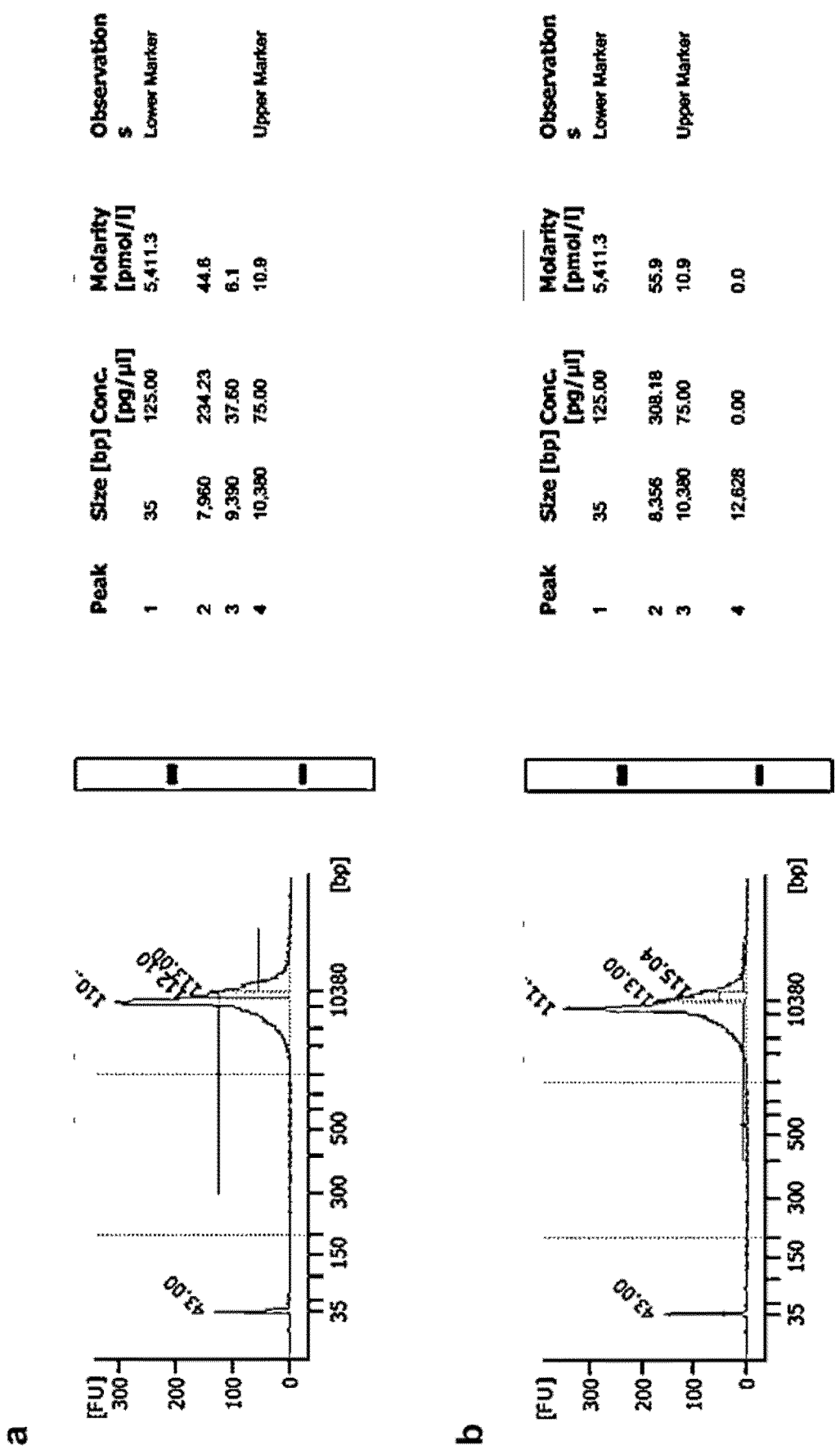
FIG. 5A-B

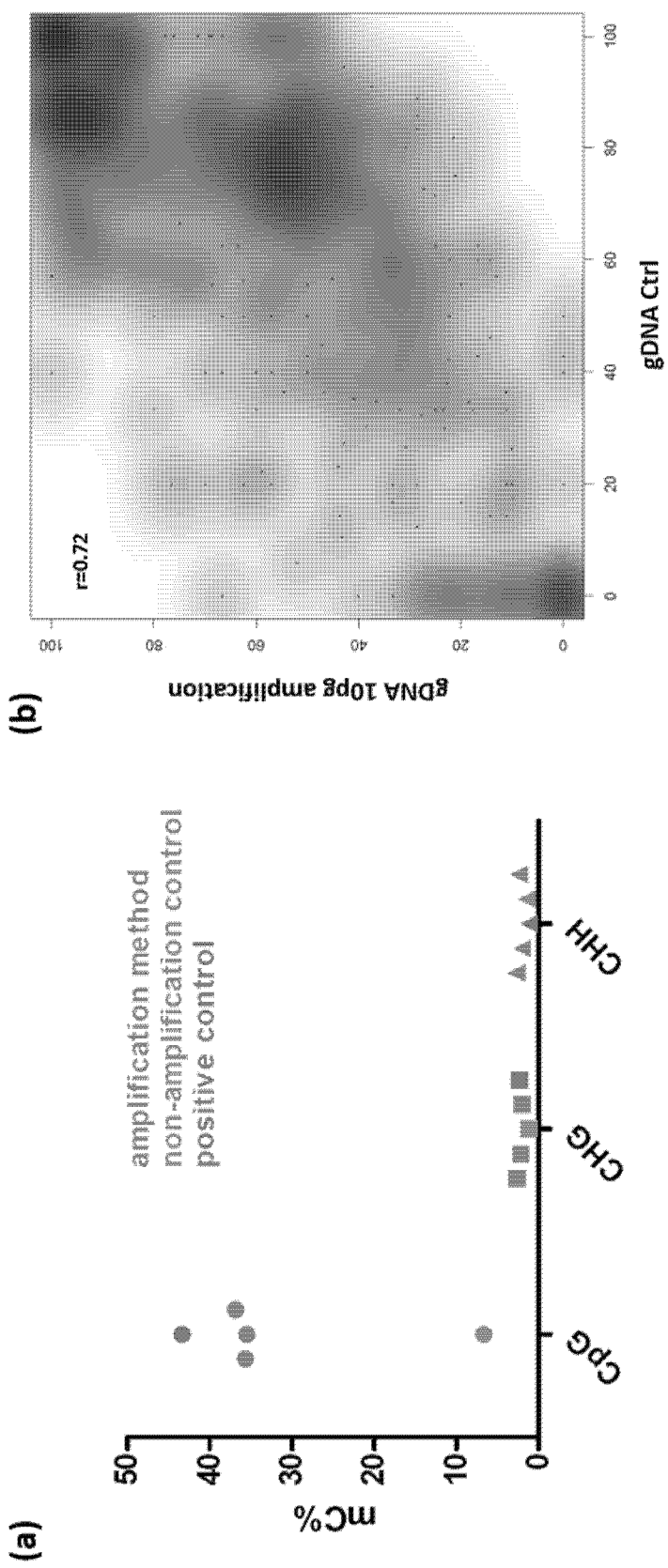
FIG. 7A-B

METHOD FOR HIGHLY SENSITIVE DNA METHYLATION ANALYSIS

CROSS-REFERENCE TO RELATED APPLICATIONS

This application is a national phase application under 35 U.S.C. § 371 of International Application No. PCT/US2018/021591 filed Mar. 8, 2018, which claims the benefit of priority of U.S. Provisional Patent Application No. 62/468,907 filed Mar. 8, 2017, all of which are hereby incorporated by reference in their entirety.

The invention was made with government support under Grant No. AR048177, awarded by the National Institutes of Health. The government has certain rights in the invention.

BACKGROUND OF THE INVENTION

1. Field of the Invention

This invention relates generally to molecular biology. More specifically, it concerns in some embodiments, compositions and methods for quantitative or single-base resolution analysis for DNA methylation (5-methylcytosine, 5mC) in limited biological samples including DNA from a low cell number or a single cell, and cell-free DNA (cfDNA) from blood or other body fluid samples, using DNMT1 coupled with strand displacement DNA polymerases to preserve 5mC information during whole genome amplification process or during amplification of specific DNA fragments or loci prior to detection by quantitative PCR or high-throughput sequencing.

2. Background Art

Genomic methylation of cytosine bases within cytosine-guanine (CpG) dinucleotides is a crucial epigenetic mechanism implicated in the regulation of cell type-specific transcriptional patterns. Consequently, the mapping of DNA methylome landscapes at single-base resolution provides a number of powerful insights as to the involvement of epigenetic regulation in development and disease. Due to the often notable extent of divergence between the methylation profiles of cells within a given population, information derived from bulk tissue samples may fail to account for epigenomic tissue heterogeneity caused by cell-to-cell variation; thus, bulk data could mask the differential contributions to biochemical processes that are achieved by individual cells. The ability to carry out single-cell whole-methylome analysis with high rates of accuracy and CpG coverage would therefore enable deconvolution of bulk samples for more in-depth study of a diverse array of biological activities in which DNA methylation plays a role, including but not limited to early embryonic development and cellular differentiation, the generation of induced pluripotent stem cells, cancer progression and metastasis, immunological host-defense responses, and neuronal plasticity.

On the other hand, the discovery of circulating cfDNA in the plasma originating from tumor in cancer patients has opened new avenues for blood-based non-invasive test for cancer detection. Yet due to the degraded small size and low concentration of cfDNA extractable from the plasma, the characterization of 5mC patterns in cfDNA has been technologically demanding. Therefore, a methylome determination method that is scalable with limited cell numbers or even at the single-cell level is additionally useful for the characterization of small or rare cell populations and minute samples of DNA such as picogram-level amounts of cfDNA as well as genomic DNA from biopsy or patients samples. The current approach provides a way to faithfully amplify the methylome from genomic DNA or cfDNA.

The most widely used technique currently employed for mapping genomic methylation is whole-genome bisulfite sequencing, which provides single-base resolution of cytosine methylation with a breadth of coverage encompassing over 90% of the nearly 29 million CpG sites in the human genome. However, while traditional bisulfite treatment procedures enable efficient methylation mapping, they concomitantly instigate the widespread degradation of the sample of interest and thus requires microgram quantities of input DNA. As a result, standard whole-genome bisulfite sequencing can hardly be scaled to the level of small number of cells or for single-cell analysis. For instance, Lorthongpanich et. al. (2013) refrained from bisulfite treatment altogether, instead combining methylation-specific restriction enzymes with quantitative PCR. While this technique enables the measurement of DNA methylation in single cells, its applicability is limited to several dozen candidate CpGs. A more potent method that amalgamates restriction enzyme treatment with bisulfite sequencing, known as reduced representation bisulfate sequencing (RRBS), was demonstrated by Guo et. al. (2013) in single cells. Such a workflow, though holding more promise, nonetheless demonstrates a limited coverage of 0.5 to 1 million CpG sites. Recently, Smallwood et. al. (2014) adapted for single-cell analysis a modified bisulfite sequencing protocol using post-bisulfite adaptor tagging, extending it with a pre-amplification step, ultimately achieving coverage of approximately 20% of CpGs per individual cell. While the CpG coverage obtained with the reported method could be enhanced to up to 48.4%, this required both the use of deep sequencing—which results in high PCR duplicate rates—and the combination of sequence data obtained from the genomic DNA of two distinct cells. Moreover, a reliable protocol for thorough and facile whole-genome methylation analysis of picogram-level samples of cell-free DNA has not yet been established in the literature. The ability to amplify genomic DNA or cfDNA while preserving its methylation status is therefore critical to performing epigenomic studies involving single cells or minute starting DNA quantities.

SUMMARY OF THE INVENTION

Kits, compositions, and methods are provided specifically designed to address the problem of low amount of starting material by utilizing an amplification step to enlarge the limited Amplification of the DNA samples with 5mC information retained is a key aspect. As shown in the Examples, in some embodiments the use of DNA methyltransferases along with strand displacement DNA polymerases to achieve simultaneous DNA amplification and methylation of the amplified hemi-methylated products produces fully methylated products.

Furthermore, the wide and various applicability of these embodiments on different biological samples with limited amount, including low amount of purified human genomic DNA, DNA from low number or a single human cell, and cell-free DNA purified from human blood or other body fluids is shown herein. Respective protocols for initial treatment and conditions adjusted to these different samples are developed in accordance.

In other embodiments, the following is provided: a method of amplifying the target DNA molecules with retained 5mC information comprising: a step of denaturing the target DNA molecule to remove secondary structures, a whole genome amplification step coupled with DNA methyltransferase adding 5mC to the semi-methylated products while they are being produced, a step of purifying the product to extract the amplified DNA with 5mC information faithfully copied from the starting material.

Other embodiments include a method of amplifying 5mC DNA as described in the preceding paragraph, and followed by sonication of the product DNA, and enrichment of DNA fragments using either a 5mC antibody or a Methyl-CpG binding protein, for example using MethylMiner™ Methylated DNA Enrichment Kit from ThermoFisher, and analysis by downstream qPCR or high-throughput sequencing.

In another embodiment there is a method of amplifying 5mC DNA as described in paragraph [0009], and followed by bisulfite treatment and subsequent purification, for example using EZ DNA Methylation-Direct™ Kit from Zymo, and analysis by either PCR using gene specific primers and Sanger sequencing to investigate the methylation status of an individual gene, or bisulfite library construction and high-throughput sequencing, for example using TruSeq DNA Methylation Kit from Illumina.

In another embodiment, there is a method of amplifying 5mC DNA as described in paragraph [0009], preceded by a step of extracting a single cell or small number of cells from a sample containing a cell population, and a cell lysis step of breaking the cell membrane to expose the DNA content for direct downstream amplification.

In yet another embodiment there is a method of amplifying 5mC DNA as described in paragraph [0009], preceded by a step of extracting cfDNA from a sample of human blood or other body fluids, quantification and calculation of exact enzyme ratio and amount to use prior to amplification steps.

In yet another embodiment, there is a method of amplifying 5mC DNA as described in paragraph [0009] to which a primase is further incorporated during the amplification step. The primase has a potent activity to synthesize DNA primers. An example of a primase is *Thermus thermophilus* (Tth) PrimPol. In embodiments, the primase lowers the bias that may be introducing during the priming step and enables near-complete whole genome amplification.

In addition, there are methods, apart from the whole genome amplification, in which the 5mC-retained system is applied to amplify specific loci with corresponding primers and and to acquire the methylation information of a particular fragment. This is particularly important to amplify specific loci with heavy methylation. In certain embodiments, the amplified products versus a control can be detected with simple detection methods, such as ELISA for example. Applications include newborn screens or other screens involving loci-specific methylation in certain diseases.

In yet another embodiment, there is a method of amplifying 5mC DNA similar as described in paragraph [0009] with the addition of corresponding primers to the specific regions of interest, preceded by a step of extracting genomic DNA from a sample of human tissue, blood or other body fluids, and followed by purification and quantification of methylation level, for example using Enzyme-Linked ImmunoSorbent Assay (ELISA).

There are methods that involve physically processing or manipulating methylated DNA in order to evaluate or analyze specific regions or on a genome-wide level. In some embodiments, a method may involve, may involve at least, or may involve at most 1, 2, 3, 4, 5, 6, 7, 8, 9, 10, 11, 12 or more of the following steps (or any range derivable therein): obtaining a biological sample, isolating DNA from a biological sample, processing a biological sample to obtain DNA from the sample; denaturing DNA; exposing DNA to alkaline conditions; separating DNA from other nucleic acids; separating methylated DNA from unmethylated DNA, separating genomic DNA from non-genomic DNA, enriching for or pooling methylated DNA or nucleic acids; isolating methylated DNA, purifying methylated DNA; discarding or not using nonmethylated DNA or nucleic acids other than genomic DNA; incubating methylated DNA with one or more nucleic acid probes or primers; incubating methylated DNA with a polymerase; incubating methylated DNA with a strand displacement polymerase; selecting methylated DNA; selecting methylated DNA and incubating the selected methylated DNA with a strand displacement polymerase; incubated methylated DNA with a polymerase under conditions that allow polymerization; incubating methylated DNA with a methyltransferase; incubating methylated DNA with a methyltransferase under conditions that allow methylation of DNA, particularly replicated unmethylated or hemi-methylated DNA; producing or reproducing methylated DNA molecules; isolating or purifying produced or reproduced methylated DNA molecules; pooling produced or reproduced methylated DNA molecules, quantifying methylated DNA or methylation of DNA; comparing methylated DNA or methylation of DNA; qualifying methylated DNA or methylation of DNA; and/or, measuring methylation of DNA or identifying methylated nucleotides or regions. It is specifically contemplated that one or more of these steps may be excluded as part of an embodiment.

In further embodiments, amplified or enriched or produced methylated DNA may be subsequently treated or manipulated using 1, 2, 3, 4, 5, 6, 7, 8 or more of the following steps: denaturing, hybridizing, fragmenting, cutting, sequencing, cloning, inserting into a plasmid or other vector, ligating, fixing, attaching, or conjugating. Linkers, primers and probes may be involved though methods are not limited as such. It is specifically contemplated that one or more of these steps may be excluded as part of an embodiment.

In certain embodiments, methylated DNA is exposed or incubated with one or more of the following reagents: polymerase, strand displacement polymerase, Phi29, a Phi29 analog or homolog, methyltransferase, DNMT1 or a related family member, analog or homolog, dNTPs, S-adenosine methionine (SAM), ligase, a nucleic acid primer or set of primers, a nucleic acid probe, nucleic acid buffer, polymerase buffer, methyltransferase buffer, restriction enzyme, methylation-specific restriction enzyme, or restriction enzyme buffer. It is specifically contemplated that one or more of these reagents may be excluded as part of an embodiment.

In some embodiments, there is a method for amplifying targeted methylated genomic DNA comprising: a) denaturing targeted methylated genomic DNA; b) incubating the targeted methylated genomic DNA with a polymerase and methyltransferase under conditions to reproduce the targeted methylated genomic DNA and create amplified genomic methylated DNA molecules; and, c) isolating the amplified genomic methylated DNA molecules. It is contemplated that the methylated DNA may be amplified or enriched by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 times (or any range derivable therein). The end DNA products may be this much more as far as number of molecules or by weight. It is contemplated that the end product may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 μg or mg or μM or mM in amount.

In another embodiments, there is a method for enriching methylated genomic DNA comprising: a) denaturing methylated genomic DNA; b) incubating the methylated genomic DNA with a polymerase and methyltransferase under conditions to reproduce the methylated genomic DNA and create amplified genomic methylated DNA molecules; and, c) enriching for the amplified genomic methylated DNA molecules using an antibody or binding protein that specifically binds methylated DNA.

In yet another embodiment, there is a method for analyzing a targeted methylated genomic sequence comprising: a) denaturing methylated genomic DNA comprising the targeted sequence; b) incubating the targeted methylated genomic DNA with a polymerase and methyltransferase under conditions to reproduce the targeted methylated genomic sequence; c) amplifying and/or sequencing the targeted methylated genomic sequence.

Other embodiments include a method for analyzing methylated genomic DNA from at least one cell in a biological sample from a patient comprising: a) extracting and denaturing methylated genomic DNA from the at least one cell; b) incubating the extracted methylated genomic DNA with a polymerase and methyltransferase under conditions to reproduce the extracted methylated genomic DNA and create amplified genomic methylated DNA molecules, wherein the polymerase and methyltransferase are present at a ratio between about 1:5 units to about 1:20 units; and, c) isolating the amplified genomic methylated DNA molecules.

In a further embodiment, there is a method for analyzing methylated cell-free DNA from a cell-free biological sample from a patient comprising: a) denaturing methylated cell-free DNA (cfDNA) from the cell-free biological sample; b) incubating the methylated cfDNA with a polymerase and methyltransferase under conditions to reproduce the methylated cfDNA and create amplified genomic methylated DNA molecules, wherein the polymerase and methyltransferase are present at a ratio between about 1:5 units to about 1:20 units; and, c) isolating the amplified genomic methylated DNA molecules.

In further embodiments, amplified methylated DNA is incorporated into vectors for a library or applied to an array or microarray for further screening or analysis. It is contemplated that the amplified methylated DNA may be affixed to the array or other physical support. Alternatively, the material may be applied to a well and used in one or more subsequent reactions including sequencing. Bisulfite sequencing is particular embodiment.

An additional embodiment includes a method for amplifying a limited amount of targeted methylated genomic DNA comprising: a) denaturing less than about 1000 picograms of targeted methylated genomic DNA; b) incubating the targeted methylated genomic DNA with a polymerase and methyltransferase under conditions to reproduce the targeted methylated genomic DNA and create amplified genomic methylated DNA molecules, wherein the polymerase and methyltransferase are present at a ratio between about 1:5 units to about 1:20 units; and, c) isolating the amplified genomic methylated DNA molecules.

In some embodiments, there is a method for amplifying methylated genomic DNA comprising: a) denaturing methylated genomic DNA; b) performing rolling circle amplification by incubating the denatured methylated genomic DNA with a polymerase, methyltransferase, and probe under conditions to create an amplified and methylated rolling circle product; and, c) detecting the methylation on the amplified and methylated rolling circle products. It is specifically contemplated that the probe is a circularizable probe or a padlock or turtle probe.

The amount of enzyme included or added may be, be at least or be at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 units (U) or micromoles (or any range derivable therein). The applies but is not limited to polymerase and methyltransferase. The enzyme may be added or be in a reaction having a volume of, of at least, or of at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 microliters, milliliters, centiliters or liters (or any range derivable therein).

In some embodiments, the ratio of polymerase units (U) to methyltransferase units (U) is between about 1:5 to about 1:20. The ratio of units of polymerase to methyltransferase may be, be at least, or be at most about 1:50, 1:45, 1:40, 1:35, 1:30, 1:25, 1:24, 1:23: 1:22, 1:21; 1:20, 1:19, 1:18, 1:17; 1:16, 1:15, 1:14, 1;13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1 or more, or any range derivable therein. In some embodiments the ratio of units added for polymerase:methyltransferase is about 1:15. That ratio may also be applied with respect to moles (pic-, nano-, or micro-) or weight (in pico-, nano- or micrograms). It is contemplated that the ratios refer temporally to when one or both enzymes are first with the substrate and under conditions to be active. Additionally, enzyme may be added at a later point in time to increase or maintain a ratio of enzymes. In some embodiments, additional enzyme may be added that is about, is at least about, or is at most about 0.01×, 0.02×, 0.03×, 0.04×, 0.05×, 0.06×, 0.07×, 0.08×, 0.09×, 0.1×, 0.2×, 0.3×, 0.4×, 0.5×, 0.6×, 0.7×, 0.8×, 0.9×, 1.0×, 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×. 3.8×, 3.9×, 4.0×, 4.1×, 4.2×, 4.3×, 4.4×, 4.5×, 4.6×, 4.7×, 4.8×, 4.9×, 5.0×, 5.1×, 5.2×, 5.3×, 5.4×, 5.5×, 5.6×,5.7×, 5.8×, 5.9×, 6.0×, 6.1×, 6.2×, 6.3×, 6.4×, 6.5×, 6.6×, 6.7×, 6.8×, 6.9×, 7.0×, 7.1×, 7.2×, 7.3×, 7.4×, 7.5×, 7.6×, 7.7×, 7.8×, 7.9×, 8.0×, 8.1×, 8.2×, 8.3×, 8.4×, 8.5×, 8.6×, 8.7×, 8.8×, 8.9×, 9.0×, 9.1×, 9.2×, 9.3×, 9.4×, 9.5×, 9.6×, 9.7×, 9.8×, 9.9×, 10.0×, 11×, 12×, 13,×, 14×, 15×, 16×, 17, 18×, 19, 20×, 21×, 22×, 23×, 24×, or 25× greater than the previous amount added or relative to the amount of another enzyme previously added or added at that time. It is contemplated that additional enzyme may be added to a reaction mix within or after 10, 20, 30, 40, 50, 60 minutes, or 1, 2, 3, 4, 5, 6, 7, 8, 9, 10, 11, 12, 13, 14, 15, 16, 17, 18, 19, 20, 21, 22, 23, 24 or more hours (or any range derivable therein). The amount added later includes any amount described herein. Additional enzyme may be added 1, 2, 3, 4, 5, 6, 7, 8, 9, 10 or more times (or any range derivable therein) before a reaction is halted or stopped.

In some embodiments, the amount of genomic methylated DNA that is incubated with the polymerase and methyltransferase is between about 5 picograms (pg) to about 1 microgram (μg). In specific embodiments, the amount of genomic methylated DNA at the start of an enzyme reaction is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 picograms, nanograms, micrograms, or milligrams or more (or any range derivable therein). Alternatively, the amount of genomic methylated DNA or total DNA in a reaction mix may be expressed as a concentration of about, about at least or about at most 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500 μg/μl or pg/μl or any range derivable therein. The amount of volume added to a reaction may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, or 1000 μl, ml, or liters or any range derivable therein. These volumes also apply to the amount of a fluid sample from a patient, which may contain cell-free DNA.

In some embodiments, the number of cells in a sample may be very limited. It is contemplated that no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 cells (or any range derivable therein) may be involved in having their genomic DNA amplified.

In further embodiments, methods involve genomic methylated DNA that is obtained from a tissue sample, a serum sample, a blood sample, a fecal sample, a urine sample, or a cheek or mouth swab. In other embodiments, genomic methylated DNA is obtained from a biological sample that is freshly prepared or may be prior-treated in any convenient way such as by fixation or freezing. In some cases fresh, frozen or fixed cells or tissues may be used, e.g. FFPE tissue (Formalin Fixed Paraffin Embedded). Thus, tissue sections, treated or untreated, may be used. Alternatively a touch imprint sample of a tissue may be used, though tther cytological preparations may be used, e.g. cells immobilized or grown on slides, or cells prepared for flow cytometry.

In some embodiments, nucleic acids are denaturing. Denaturing involves alkaline denaturation in certain cases.

Methods and kits may involve one or more polymerase enzymes. In most embodiments, the polymerase is a strand displacement polymerase. Phi29 and Phi29 variants may be used as a strand displacement polymerase. Variants include those identified in US Patent Publication 20170015980, which is hereby incorporated by reference. Bst polymerase is another one that is used.

Some embodiments of methods and kits involve a methyltransferase that can install 5-methylcytosine (5mC) on hemi-methylated DNA to a fully methylated state. In certain embodiments, the methyltransferase is DNMT1 (DNA (cytosine-5)-methyltransferase 1), which may be human DNMT1, or it may be from another mammalian source, such as a mouse. Another embodiment might include M.SssI DNMT. US Patent application publication 20140363815 provides additional information about DNMT, which is specifically incorporated by reference.

In some aspects the kits include an enzyme comprising a primase and polymerase function to synthesize primers in the DNA amplification step. An example of such an enzyme is a dual primase/polymerase (primpol) from *Thermus thermophilus*. Other enzymes such as primases are known to a person of skill in the art.

In some cases, methods involve preparing a master mix separate from an enzyme mix comprising the polymerase and methyltransferase prior the methylated DNA with the enzymes under conditions to polymerize and methylate nucleic acids. In other embodiments, primases are added to the master mix to synthesize primers during the amplification step. Kits may include a master mix separate from an enzyme mix. In some embodiments, a polymerase is not incubated with a methyltransferase for more than 1, 2, 3, 4, 5, 6, 7, 8, 9, 10 minutes or more (or any range derivable therein). Temperatures at which reagents, a master mix, one or more enzymes or an enzyme mix may be maintained or kept include—70, −20, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 Centigrade or Fahrenheit for 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or any range derivable therein.

In some embodiment a reaction is conducted at temperatures of, of at least, or of at most 15, 16, 17, 18, 19, 20, 21, 22, 23, 24, 25, 26, 27, 28, 29, 30, 31, 32, 33, 34, 35, or 40° C. or more, though it is specifically contemplated that temperatures may be in the range of 30° C. to 40° C., particularly at about 37° C.

In some embodiments, a reaction or enzyme mix comprises a methyl cofactor. In some cases, the methyl cofactor is S-adenosyl methionine (SAM). In additional embodiments, a kit and/or master mix includes dNTPs, DNA buffer and/or magnesium or a magnesium salt. In other embodiments, genomic methylated DNA and random primers are added to the master mix prior to mixing the master mix with the enzyme mix. In a kit, there may be one or more probes, primers, sets of primers, which may be random primers.

In some embodiments, methods may also involve adding more methyl cofactor after more than 3 hours of the start of incubation. In some embodiments, the amount of methyl cofactor added initially or added at a later time is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200 microliters or centiliters of cofactor at a concentration of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500 µM or mM or M (or any range derivable therein).

In additional embodiments, methods may also involve deactivating the polymerase and/or methyltransferase.

The source of the methylated DNA is not limiting. In some embodiments, it is from a patient, who may be human or another mammal or animal. In some cases, the biological sample may be from a human or other mammal or bird or fish or other animal, but the methylated DNA molecule is from a difference source such as a microbe. In some methods, there is an additional step of obtaining a biological sample from the patient comprising the genomic methylated DNA. The biological sample may be a tissue sample, a blood or serum sample, fecal sample, urine sample, or a cheek or mouth swab.

In some embodiments, methods comprise treating reproduced methylated DNA molecules with bisulfite. The molecules may or may not be isolated. In some embodiments, methylated DNA products may be sequenced. In other cases, methods may involve detecting or identifying 5-methylcytosine in the isolated reproduced methylated DNA molecules.

In some cases, methods involve denaturing the amplified genomic methylated DNA molecules. In other embodiments, methods include sonicating the methylated DNA molecules, which may be amplified and/or purified or isolated. In additional cases, there is also a step of enriching for genomic methylated DNA molecules, which may be an amplified pool of molecules and/or may be denatured. In some cases, enriching for denatured amplified genomic methylated DNA molecules involves a 5mC antibody or a methyl-CpG binding protein.

One of the reasons the embodiments disclosed herein are needed is to allow for analysis of genomic methylated DNA. Embodiments include analyzing the enriched denatured amplified genomic methylated DNA molecules. Methylated DNA may be analyzed or evaluated in a number of ways, including, but not limited to those set forth according to US patent application publications 20160115525, 20140178881, 20150056616, 20150056616, 20140004511, which are hereby incorporated by reference. Additionally or alternatively, other commercially available methylation quantification or detection kits/reagents may be used, such as by ThermoFisher, Enzo Life Sciences, EpiGentek. Abcam, Slgman-Aldrich, Zymo (among others) or a Bioanalyxer (Agilent) may be implemented. Analyzing the enriched denatured amplified genomic methylated DNA molecules include but are not limited to these procedures or assays: quantitative PCR, sequencing, or an array-based analysis. Other examples include using qPCR, an array, sequencing, methylation-sensitive restriction enzyme digestion, SMRT, high throughput sequencing, or nanopore. In some embodiments, detecting enriched methylated DNA can be accomplished with qPCR, array, sequencing (after bisulfite) or other approaches, including but not limited to methylation-sensitive restriction enzyme digestion (using restriction enzymes that cleave DNA at specific unmethylated-cytosine residues while leaving methylated-cytosine residues intact, such as HpaII and MspI for 5mC detection within CCGG recognition site); SMRT sequencing (single molecule, real time sequencing developed by Pacific Biolab using zero-mode waveguides and phospholinked nucleotides to detect DNA bases while the DNA polymerase producing a natural DNA strand); and nanopore sequencing (detecting the order of DNA nucleotides while the DNA strand is controlled to pass through a nanopore and cause changes in the ionic current levels).

In some embodiments, methods involve amplifying and/or sequencing one or more target genomic regions using at least one pair of primers specific to the target genomic regions. In certain embodiments, the primers are heptamers. In other embodiments, enzymes are added such as primases or primase/polymerase combination enzyme to the amplification step to synthesize primers.

Additional embodiments concern preparing a library from the amplified genomic methylated DNA molecules. In other embodiments, methods involve lysing one or more cells from a biological sample from a patient. In other cases, methods involve extracting DNA from a biological sample from a patient.

Embodiments also include one or more kits comprising, in suitable container(s), 1, 2, 3, 4, 5, 6, 7, 8 or more of the following: strand displacement polymerase, Phi29 or a variant thereof, DNMT1, human or mouse DNMT1, S-adenosine methionine, dNTPs, random primers, and one or more nucleic acid buffers, magnesium or a magnesium salt, or BSA. In some cases the kits include an enzyme comprising a primase and polymerase function to synthesize primers in the DNA amplification step. An example of such an enzyme is a dual primase/polymerase (primpol) from *Thermus thermophilus*.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2. Test regions selection and design of primers. Two genome regions with different methylation patterns are displayed along with regions of complementary primer binding (shown as arrows). NFATC1 locus is selected as the hypermethylated test region with 20 confirmed 5mCpG sites, while MAPK8IP2 locus is selected as the unmethylated test region with 21 confirmed unmethylated CpG sites.

FIG. 4A-B. Optimization data of 5mC-WGA reaction using different enzyme ratios (a) and input DNA amounts (b). Except for the reaction component being optimized, all the rest of the reaction components stay the same as described in the preferred embodiments section. The results are evaluated using bisulfite treatment and Sanger sequencing. 'C' reads in the hypermethylated locus denote accuracy of 5mC copying; while 'T' reads in the unmethylated locus denote elimination of de novo 5mC incorporation.

FIG. 5A-B. Sonicated gDNA (a) and cell-free DNA (b) amplification profiles after 5mC-WGA reaction analyzed by Bioanalyzer. Purple and green signify upper and lower molecular markers. Main products after 5mC-WGA in two groups both largely converge with or exceed the upper marker region, indicating successful >10 kb amplification.

FIG. 7A-B. Global DNA methylation level in a CpG (CG) and non-CpG (CHH/G) context for 10 pg genomic DNA amplified samples and the bulk sample as the positive control (a) confirmed the retainability of the methylome during the amplification. (b) Pearson correlation of methylated CpG sites for 10 pg genomic DNA amplified samples and control sample BS-seq datasets. Pearson analysis of BS-seq datasets for amplified samples and the positive control demonstrated high correlation of the methylated CpG sites acquired with the high-throughput sequencing.

DETAILED DESCRIPTION OF THE EMBODIMENTS

Figure 1:
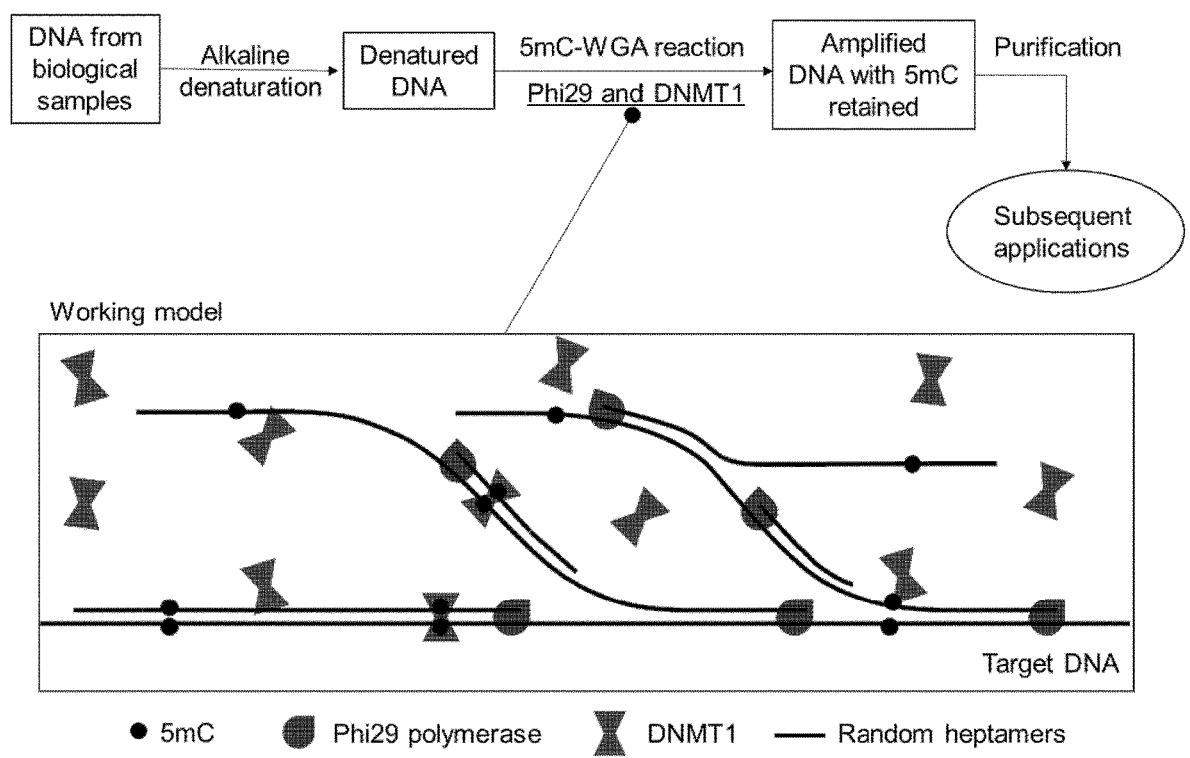
FIG. 1. A flow chart showing the processing steps of 5mC-WGA, with model of co-functioning of Phi29 and DNMT1. As shown in the model, DNMT1 adds new 5mC based on the template 5mC patterns at the double strand DNA regions synthesized by Phi29, so that the 5mC marks are faithfully copied during DNA amplification. The optimal enzymatic ratio between Phi29 and DNMT1 ensures DNMT1 has ample time to add 5mC before double strands are displaced by a new working Phi29.

The present disclosure relates to the methods and kits for manipulating, producing, creating, amplifying purifying, isolating, analyzing, assaying, measuring, sequencing, and evaluating methylation of nucleic acids, particularly genomic DNA. What is provided is a way to amplify DNA from very limited biological samples (e.g. from small number of cells, body fluids, or biopsy samples) with DNA methylation (5-methylcytosine, 5mC) information faithfully copied from the starting material. A step for processing the DNA into unstructured form from various biological samples while being compatible with subsequent enzymatic reactions; a step for amplifying the template DNA molecules while copying the 5mC patterns of template into the product DNA molecules; a step of purifying the enzymatic reaction and prepare the amplified products for downstream applications. An enzymatic reaction system comprising of salts, S-adenosyl-methionine (SAM), deoxynucleotide triphosphates (dNTPs), random primers, and a mixture of a DNA polymerase with strand displacement activity and a DNA methylation-maintenance enzyme at an exact ratio.

It is generally desirable to be able sensitively, specifically, qualitatively and/or quantitatively to detect methylated DNA, and in particular genomic DNA, in a sample, including for example in fixed or fresh cells or tissues or in a cell free biological sample. It may be particularly desirable to detect, sequence, or evaluate methylated DNA in a single cell. For example, in population-based assays that analyze the content of many cells, molecules in rare cells may escape detection due to the low abundance of material to evaluate. This is similarly true for cell-free biological samples.

The sample may, for example, be derived from a tissue or organ of the body, or from a bodily fluid. Such a sample will advantageously be or comprise a cell or group of cells such as a tissue. The sample may, for example, be a colon, lung, pancreas, prostate, skin, thyroid, liver, ovary, endometrium, kidney, brain, testis, lymphatic fluid, blood, plasma, urinary bladder, or breast sample, or comprise colon, lung, pancreas, prostate, skin, thyroid, liver, ovary, endometrium, kidney, brain, testis, lymphatic fluid, blood, urinary bladder, or breast cells, groups of cells or tissue portions. Samples may be cultured or harvested or biopsied cell or tissue samples, e.g. as mentioned above, in which the methylated genomic DNA may be detected to reveal the qualitative or quantitative nature of the methylation that it is present, or the nucleotide sequence of methylated nucleic acids at one or more specific genes, regions, CpG islands and the like. The sample of cells may be freshly prepared or may be prior-treated in any convenient way such as by fixation or freezing. Accordingly, fresh, frozen or fixed cells or tissues may be used, e.g. FFPE tissue (Formalin Fixed Paraffin Embedded). Thus, tissue sections, treated or untreated, may be used.

A "CpG island" as used herein refers to regions of DNA with a high G/C content and a high frequency of CpG dinucleotides relative to the whole genome of an organism of interest. Also used interchangeably in the art is the term "CG island." The 'p' in "CpG island" refers to the phosphodiester bond between the cytosine and guanine nucleotides.

DNA may be isolated from an organism of interest, including, but not limited to eukaryotic organisms and prokaryotic organisms, preferably mammalian organisms, such as humans.

DNA methyltransferases (MTases) that transfer a methyl group from S-adenosylmethionine to either adenine or cytosine residues, are found in a wide variety of prokaryotes and eukaryotes.

In certain aspects, the step of enriching a sample for sequences comprising CpG islands can be done in different ways. One technique for enrichment is immunoprecipitation of methylated DNA using a methyl-Cytosine specific antibody (Weber et al., 2005). Alternatively, an enrichment step can comprise digesting the sample with a one or more restriction enzymes which more frequently cut regions of DNA comprising no CpG islands and less frequently cut regions comprising The terms "target", "target sequence", "target region", and "target nucleic acid," "target DNA" etc. are used synonymously herein and refer to the nucleic acid, or to a region or sequence thereof, which is to be detected or to which a reagent used in the method binds, for example the methylated DNA to be detected, or more particularly the regions thereof, to which a probe is hybridized or primers hybridize or amplify. Thus a target sequence may be within a gene or outside a gene or in a coding region or a noncoding region. As discussed above, the methylation may be genomic DNA that includes one or more CpG islands. In some embodiments, multiple CpG islands are targeted.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989.; Wetmur, 1991; and Owczarzy et al., 2008, which are incorporated herein by reference). Thus the design of appropriate primers and probes, and the conditions under which they hybridize to their respective targets is well within the routine skill of the person skilled in the art.

Methods involve a polymerase that replicates methylated genomic DNA. Strand displacement polymerase are used in some embodiments. DNA polymerase such phi29 (φ29) polymerase, Klenow fragment, *Bacillus stearothermophilus* DNA polymerase (BST), T4 DNA polymerase, T7 DNA polymerase, or DNA polymerase I may be used.

In certain aspects, methods also involve incorporation of a primase with potent activity in the amplification step to synthesize DNA primers, such as for example a primase/polymerase from *Thermus thermophilus* (Tth) PrimPol, so as to lower the bias introduced during priming step and enable near-complete whole genome amplification.

In some embodiments, methods involve amplifying and/or sequencing one or more target genomic regions using at least one pair of primers specific to the target genomic regions. In certain embodiments, the primers are heptamers. In other embodiments, enzymes are added such as primases or primase/polymerase combination enzyme to the amplification step to synthesize primers.

An example of an enzyme with dual activity is an enzyme with primase and polymerase function (primpol) is obtained from the thermophilic bacteria *Thermus thermophilus*. The enzyme combines two distinct and complementary activities in a single thermo-stable protein: primase and polymerase. The enzyme creates its own primer sequence.

PrimPol from *T. thermophilus* shows a great tolerance to damaged DNA. DNA is subject to chemical modifications within the cells. PrimPol has the ability to introduce a variety of substrate nucleotides (e.g. fluorescent nucleotides) into DNA and RNA template molecule. PrimPol has a role in multiple displacement amplification (MDA) reactions, generating primers for its subsequent use by Phi29 DNA polymerase, thus making unnecessary the use of random synthetic primers and possibly resulting in a more uniform amplification of DNA.

Primases are enzymes known in the art, such as for example bacterial T7 primase. T7 is used to amplify genomic DNA. However, it is has been used with a method involving low throughput sequencing and qPCR, and with a starting material of at least 1 ng gDNA. This is much larger volume than what is taught in the current disclosure.

Rolling circle amplification is known in the art. Upon the hybridization of the terminal regions of a padlock probe to a complementary cDNA sequence, the padlock probe is "circularized" by ligation. The circularization of the padlock probe(s) may be carried out by ligating, directly or indirectly, the ends of said padlock probe(s). Procedures, reagents and conditions for this are well known and described in the art and may be selected according to choice. In specific embodiments, the in the circularization of the padlock probe(s) step, the terminal regions of the padlock probe may hybridize to non-contiguous regions of the cDNA such that there is a gap between said terminal regions.

The term "library" refers to a collection (e.g., to a plurality) of vehicles that comprise the amplified genomic methylated DNA molecules. The vehicle may be a vector, construct, array, or other physical vehicle. A "vector" or "construct" (sometimes referred to as gene delivery or gene transfer "vehicle") refers to a macromolecule, complex of molecules, or viral particle, comprising a polynucleotide to be delivered to a host cell, either in vitro or in vivo. The polynucleotide can be a linear or a circular molecule. One of skill in the art would be well equipped to construct a vector through standard recombinant techniques (see, for example, Maniatis et al., 1988 and Ausubel et al., 1994, both incorporated herein by reference). An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

Example 1

Reaction Set-up

This invention is directed to a method of amplifying the target DNA molecules with retained 5mC information comprising:
(a) a step of denaturing the target DNA molecule to remove secondary structures,
(b) a whole genome amplification step coupled with DNA methyltransferase adding 5mC to the semi-methylated products while they are being produced,
(c) a step of purifying the product to extract the amplified DNA with 5mC information faithfully copied from the starting material.

The design of the workflow is shown in FIG. 1 and describe in details below:
(a) Alkaline denaturation of genomic DNA, for example using REPLI-g Mini Kit from Qiagen.

First prepare buffers: Prepare Buffer D1 by adding 16 ul water to 4.5 ul Buffer DLB and Buffer N1 by adding 42.5 ul water to 7.5 ul Stop Solution.

Then dilute genomic brain DNA to a concentration of 200 pg/ul. Add 9 ul water to 1 ul diluted genomic DNA (200 pg). Add 10 ul Buffer D1 to genomic DNA, vortex and briefly centrifuge the mixture, and incubate at room temperature for 3 minutes.

Add 20 ul Buffer N1 to the denatured genomic DNA, then vortex and briefly centrifuge the mixture.

The final DNA concentration of the solution is 5 pg/ul. For each 5-pg input reaction, add 5 ul random heptamer primer stock (for example, from ThermoFisher) to 1 ul denatured gDNA and place on ice.

(b) Whole genome amplification step coupled with DNA methyltransferase, for example use Phi29 as polymerase and human DNMT1 as methyltransferase, both from NEB.

First prepare a WGA master mix on ice based on the following single-reaction volumes: 5 ul 10×Dnmt1 Buffer, 1.67 ul 10 mM dNTPs, 0.5 ul 100×BSA, 0.5 ul 1 M MgCl2, 0.5 ul 1 M (NH4)2SO4, 17.83 ul water, totaling 26.00 ul.

Then aliquot the master mix into the appropriate number of reactions, and add 6 ul genomic DNA/primer mix to each.

Next prepare WGA enzyme mix on ice based on the following single-reaction volumes: 15 ul DNMT1 [30 units]; 1.0 ul 32 mM SAM; 2 ul of 10×Phi29 dilution [2 units]. Note that do not combine the enzyme mix with the above master mix yet, as Phi29 polymerase is maximally active at a lower temperature than Dnmt1 and reaction coupling may be lost.

Finally finish the setup of the 5mC-WGA reaction by first equilibrate enzyme-less reaction mixes and enzyme mixes at 37° C. for 5 minutes, then add reaction mixes to corresponding enzyme mixes. Incubate reactions at 37° C. for 10 hours, adding 0.5 ul 32 mM fresh SAM to each reaction after 5 hours. Then heat-inactivate DNMT1 and Phi29 polymerase for 20 minutes at 65° C., and hold reactions at 4° C. after completion.

(c) Purification of the product. Using magnetic beads-based protocol is preferred than column-based method, as the size of the product is larger than 10 kb. For example, using Ampure XP beads from Beckman. Adding beads with the reaction with 1:1 ratio in volume, mix well and incubate at room temperature for 15 minutes, wash with 200 ul of 80% ethanol for two times without disturbing the beads, dry the beads at room temperature for 5 minutes, then elute with 20 ul nuclease-free water. The purified products are now ready to be used in the downstream applications. The present invention will be next more specifically described by way of Examples, which will not be construed as limiting the invention.

(d) IF the system includes primases. With alkaline denaturation and the purification remain the same, the workflow is only modified during the amplification step with the addition of the primase. For example, with TruePrime WGA kit, prepare a 20 ul reaction with 1.0 ul denatured DNA; 1.0 ul 10 mM dNTPs; 2.0 ul Reaction Buffer provided; 0.5 ul 32 mM SAM; DNMT1 [20units]; 0.3 ul 10× Enzyme 2 dilution and 1.0 ul 20× Enzyme 2 dilution, replenishing with water. Incubate reactions at 37° C. for 5 hours, followed by heat-inactivate DNMT1 and Phi29 polymerase for 20 minutes at 65° C., and hold reactions at 4° C. after completion.

(1) Bisulfite treatment and Sanger sequencing to detect 5mC patterns of differentially methylated genes after 5mC-WGA amplification of pico grams of human gDNA.

In this example, the efficiency and accuracy of genomic 5mC amplification by 5mC-WGA are evaluated.

Example 2

Bisulfite Treatment of 5mC-WGA Product

Bisulfite treatment is carried out with commercial kits, for example using EZ DNA Methylation-Direct™ Kit from Zymo. 20 ul of 5mC-WGA product is mixed with freshly prepared CT Conversion Reagent solution in a PCR tube, boiled at 98° C. for 8 minutes, followed by incubation at 64° C. for 3.5 hours, then returned to 4° C. The reaction is then purified using the standard column provided in the kit. Note that at this step the products can be quantified using Qubit ssDNA kit (ThermoFisher). For input <50 pg the typical amplification can be over 1,000 fold.

Example 3

Detect 5mC Patterns of Differentially Methylated Genes by Sanger Sequencing

The purified bisulfite converted product is further subjected to PCR amplification of specific genomic regions using hot start DNA polymerase, for example ZymoTaq™ DNA Polymerase from Zymo. Example genomic regions, their methylation patterns and bisulfite-specific primer designs are shown in FIG. 2. The sequence of the primers are listed below.

```
NFATC1-For
                                       (SEQ ID NO: 1)
TTTTTTGTAATAAGAGGAAGTATAGTTTTA

NFATC1-Rev
                                       (SEQ ID NO: 2)
ATCTCCCAAATCCAAACTACTATC (hypermethylated)

MAPK8IP2-For
                                       (SEQ ID NO: 3)
GGTTGTGTAGTTTTTATTGAGTGTTTA

MAPK8IP2-Rev
                                       (SEQ ID NO: 4)
AATCCCCCCAAAAACCCTAAC (unmethylated)
```

Figure 3:
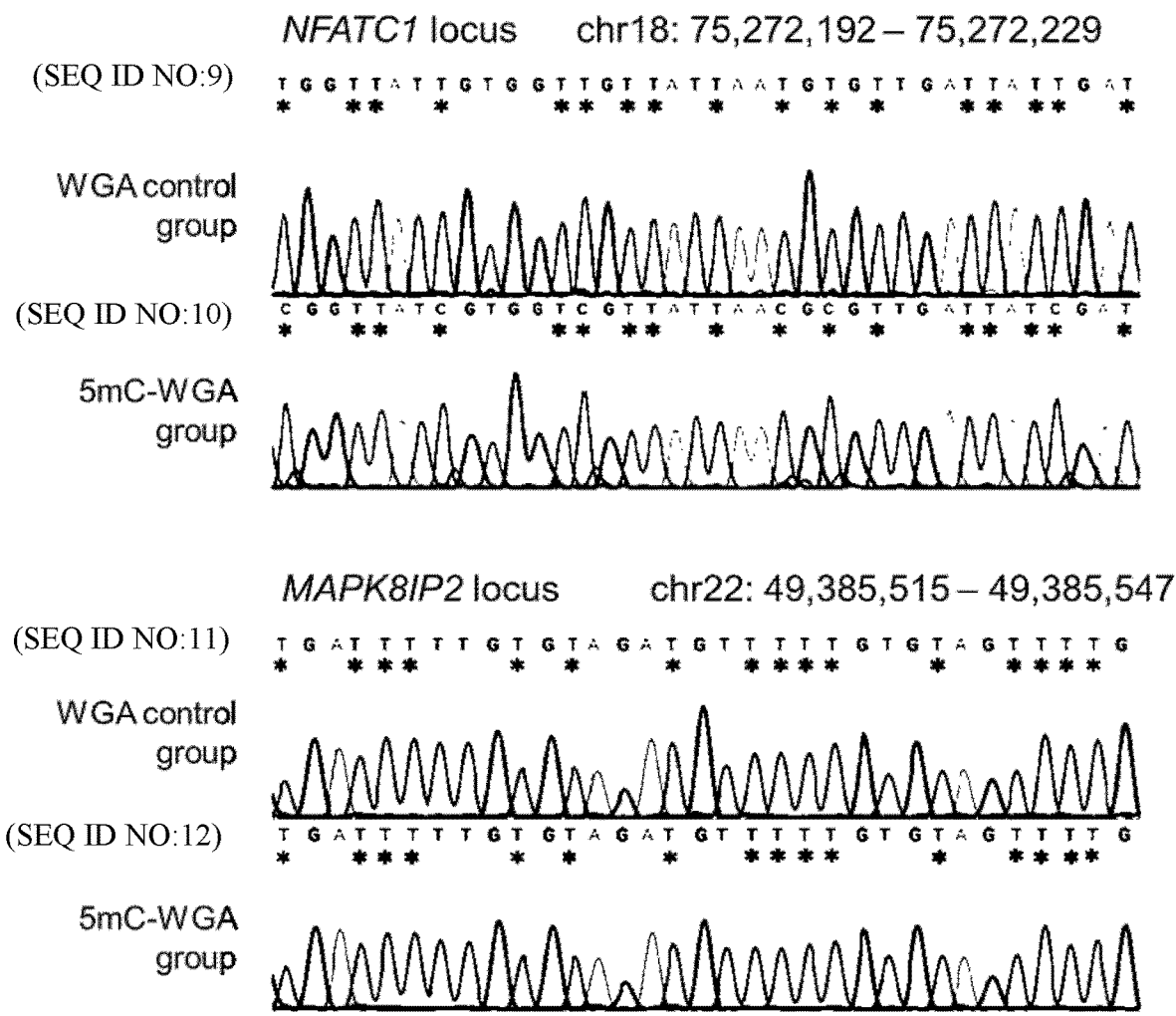
FIG. 3. Bisulfite treatment and Sanger sequencing data of the amplified test regions. At known 5mCpG sites in the hypermethylated region (last 6 sites of NFATC locus are shown), unlike WGA control group, all 5mCpG sites have been retained in the amplified product of 5mC-WGA group (blue peaks), indicating efficient 5mC copying activity of this method. At known unmethylated CpG sites in the unmethylated region (last 5 sites of MAPK8IP2 locus are shown), both WGA control and 5mC-WGA groups show complete C to T conversion, indicating minimal false positive de novo methylation activity of this method. Each reaction shown here utilized 5 pg human brain gDNA as the template and the same reaction composition described in the preferred embodiments section, with the only exception that WGA control groups use no DNMT1. Black asterisks indicate bases that are non-CpG cytosines in the unconverted gDNA sequence; pink asterisks denote CpG cytosines in the unconverted gDNA sequence.

1-4 ul converted product is used as template for PCR amplification, accompanied by 25 ul ZymoTaq™ PreMix, 5 ul gene specific primer mix (10 uM), and nuclease-free water up to 50 ul total volume. The PCR reaction is carried out with the following protocol: Initial denaturation at 95° C. for 10 min, then a cycle of denaturation at 95° C. for 30 sec, annealing at 55° C. for 30 sec, extension at 72° C. for 60 sec for a total of 40-50 cycles, and a final extension step at 72° C. for 7 min followed by 4° C. holding for >4 min. Completed PCR is then purified using either spin column-based or magnetic beads-based clean up protocol. The purified products are analyzed with Sanger sequencing using corresponding forward primers. Example results are shown in FIG. 3. Sequence reads as 'C' indicate 5mC methylated sites, reads as 'T' indicate unmethylated sites, while reads as 'N' or 'Y' indicate 5mC sites that are not completely maintained after amplification, or a de novo site added by DNMT1.

Example 4

Study of the Optimal Enzymatic Ratio of DNMT1 and Phi29 and Input Amount

To optimize the coupled enzymatic reactions of DNMT1 and Phi29, different ratios of the two enzymes are used to perform the 5mC-WGA reaction, with the efficiency evaluated by bisulfite treatment and Sanger sequencing described above. 10 ng of human brain gDNA is used as the input sample, different enzyme ratios ranging from 1:4 to 1:15 are used, with rest of experimental steps identical from the previously described protocol. The results are shown in FIG. 4a. The results indicate Phi29:DNMT1=1:15 as the optimal enzyme ratio.

To evaluate the versatility of 5mC-WGA for different input DNA amounts, 5 pg-10 ng human brain gDNA are used in 5mC-WGA with the optimal enzyme ratio. The results are shown in FIG. 4b. The results indicate 5mC-WGA is suitable for different input DNA amounts from 10 ng (and above) to 5 pg (amount of DNA from a single cell) with stable performance.

(2) Using Other Forms of Biological Samples for 5mC-WGA.

The applicability of other forms of biological samples to be used directly for 5mC-WGA amplification is discussed in this example. More specifically, the option of using cells directly as input sample for 5mC-WGA, and the option of using cell-free DNA extracted from body fluids (e.g. blood) as input sample for 5mC-WGA, are demonstrated.

Example 5

Use Cell-Free DNA as 5mC-WGA Input Sample

Cell-free DNA extracted from body fluids is generally present at very low abundance and partially degraded, causing major technical difficulties to detect its methylation patterns which contain valuable diagnostic information. The applicability of using cell-free DNA directly as 5mC-WGA input sample is demonstrated. First, a control group using 1 ng mouse gDNA sonicated to ~300 bp is used as the input sample for 5mC-WGA reaction to ensure the efficiency of amplification of fragmented DNA. The product is purified and analyzed using Bioanalyzer (Agilent), with result showing efficient amplification (FIG. 5a). Next, 100 pg of cell-free DNA extracted from pancreatic cancer patient blood (~200 bp) is used in the 5mC-WGA reaction. The purified product is analyzed with Bioanalyzer (Agilent). The profile shown in FIG. 5b resembles the sonicated gDNA profile, which indicates cell-free DNA can be directly used as input sample of 5mC-WGA for efficient amplification.

Example 6

Use Cells as 5mC-WGA Input Sample

In addition to using purified DNA as the input sample for 5mC-WGA, processed cells can be used directly in 5mC-WGA, skipping extra purification steps and facilitating low cell number or single cell detection applications.

Extracted cells need to be first lysed before being added into the reaction. The compatible lysis protocol is described here: Prepare two buffers used in the lysis protocol, buffer L (400 mM KOH, 10 mM EDTA, 100 mM DTT) and buffer N (200 mM HCl, 300 mM Tris pH7.5). To the extracted cells (1-15 cells, scale up for more cells), add 5 ul buffer L, incubate on ice for 10 min. Then add 5 ul buffer N, mix well. The lysate can now be added into a 5mC-WGA reaction for amplification of DNA and 5mC patterns.

(3) MeDIP-Seq of Pico Grams of Human Brain gDNA Using 5mC-WGA Method

DNA amplified using 5mC-WGA can be further analyzed with high-throughput sequencing to reveal genome-wide 5mC patterns, either in clusters (by MeDIP-seq) or at single-base resolution (by Whole-Genome Bisulfite Sequencing, WGBS).

For MeDIP-seq, the purified DNA can be sonicated and subjected to the processing with commercial MeDIP and DNA NGS library construction kits. Here we use KAPA HyperPlus and ThermoFisher MethylMiner kits as an example to demonstrate the workflow.

Example 7

Sample Preparation 100 pg human brain gDNA is used as the input sample for 5mC-WGA amplification according to the protocol described previously. The product is purified and the concentration is measured with Nanodrop. Both amplified product and template DNA (as positive control) are used for MeDIP-seq library construction.

Example 8

DNA Processing Before MeDIP

Example use of KAPA HyperPlus kit for pre-MeDIP processing of DNA.

DNA fragmentation: 100 ng purified 5mC-WGA product and template DNA are subjected to enzymatic fragmentation according to manufacturer's protocol. 14 ul DNA is mixed with 2 ul fragmentation buffer and 4 ul fragmentation enzyme mix, incubated at 37° C. for 30 min, then the reaction is quenched on ice.

End repair and A-tailling: 20 ul mixture from last step is supplemented with 2.8 ul end repair buffer and 1.2 ul enzyme mix, incubated at 65° C. for 30 min, then left at room temperature for 5-10 min for better repairing.

Adaptor ligation: 24 ul mixture from last step is supplemented with 1.2 ul index (25 uM, Bioo), 12 ul ligation buffer, 4 ul ligase, and nuclease-free water up to 44 ul. The reaction is kept at 20° C. for 60 min, followed by Ampure beads purification with 1:1 volume ratio. The processed DNA is now ready to be enriched with MeDIP.

Example 9

5mC DNA Enrichment with MeDIP

Example use of ThermoFisher MethylMiner kit for MeDIP enrichment of methylated DNA fragments.

Follow the manufacturer's protocol, first prepare the magnetic beads and couple the MBD-biotin protein. Then incubate MBD-beads with processed DNA generated from the previous steps, using the protocol for 5 ng-1 µg input DNA. Finally remove the uncaptured DNA and elute the captured, 5mC-containing DNA fragments. These enriched products are now ready for library amplification.

Example 10

MeDIP-seq Library Amplification

Example use of KAPA HyperPlus kit for post-MeDIP amplification of DNA library.

qPCR of the enriched DNA fragments: To determine the accurate number of PCR cycles needed for amplifying the MeDIP library, 1 ul of template DNA or MeDIP enriched DNA is used in a 20 ul qPCR reaction containing 10 ul qPCR master mix (e.g. Roche FastStart SYBR Green) and 2 ul primer mix. The cycle number generating enough library is determined and used in the subsequent PCR reaction.

Amplification of MeDIP libraries: Based on the cycle numbers determined by qPCR, a 50 ul reaction containing template or enriched DNA, 25 ul KAPA HiFi HotStartReadyMix, and 5 ul primer mix is prepared and amplified in a thermal cycler. The products are further purified and subjected to NGS-sequencing.

Figure 6:
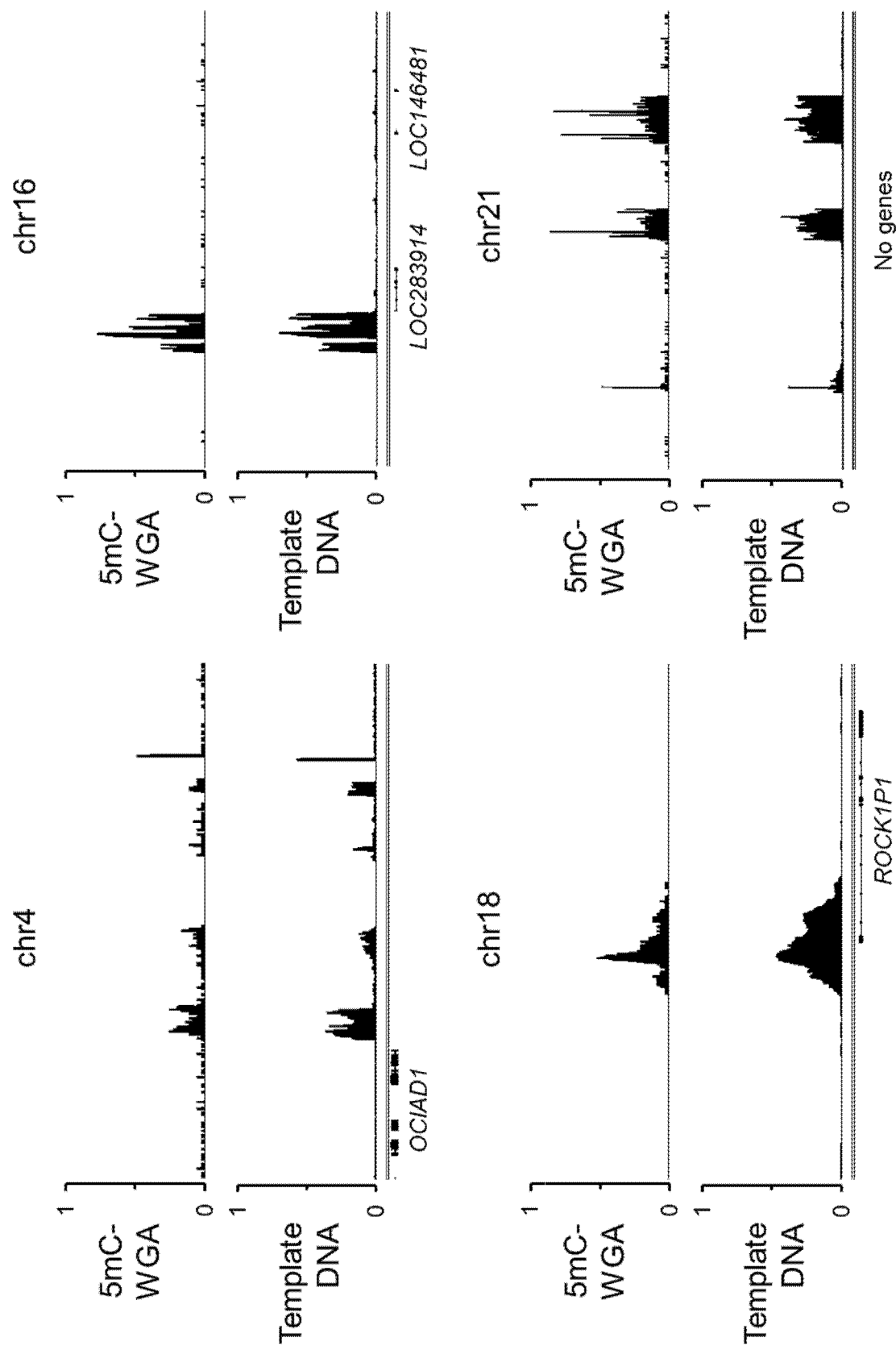
FIG. 6. MeDIP peak patterns at example sites identified in 5mC-WGA sample and template DNA sample. Similar patterns are observed in both groups, indicating efficient genome-wide 5mC copying during 5mC-WGA.

The resulting data demonstrate good maintenance of genome-wide 5mC patterns using 5mC-WGS. A few example regions are shown in FIG. 6.

(4) WGBS of 5mC-WGA Amplified DNA from Limited Biological Samples.

For WGBS, the purified DNA is first subjected to bisulfite treatment, followed by processing using commercial WGBS library construction kits. Here we use Illumina TruSeq DNA Methylation kit as an example to demonstrate the workflow.

Example 11

Bisulfite Treatment of 5mC-WGA Product

Same with the protocol described in the first example. Note EZ DNA Methylation-Gold and EZ DNA Methylation-Lightning kits from Zymo can be used as alternative options.

Example 12

WGBS Library Construction

Example use of Illumina TruSeq DNA Methylation kit for WGBS library construction from bisulfite treated 5mC-WGS products.

Follow the manufacturer's protocol, first anneal the DNA synthesis adaptors to the denatured ssDNA, then synthesize complementary DNA strand to produce dsDNA product, next tag the dsDNA with known adaptor sequences at both ends, finally amplify the library with specific indexes sequences for multiplexed NGS-sequencing.

Example 13

5mC-Retained Amplification of Specific Loci from Limited Biological Samples

The reaction for specific loci with methylated sites retained is only different from the one for whole genome amplification with the addition of 4 ul both forward and reverse primers (10 nM) of the region of interest. Example use is the amplification of the FMR1 gene as a potential diagnosis of Fragile X Syndrome. Corresponding primers are:

FMR1 Forward GCTCAGCTCCGTTTCGGTTT-CACTTCCGGT (SEQ ID NO:5)

FMR1 Reverse CCTCCATCTTCTCTTCAGCCCT (SEQ ID NO:6)

The reaction is prepared also with 8 ul primer pairs (each one at 5 nM) and incubated based on the same thermocycle.

Preferred embodiments of this invention are described herein, including appropriate examples known to the inventors for the application of this invention. The applications described above are exemplary only, and should not be considered as limiting the scope of this invention.

REFERENCES

Lorthongpanich, C., Cheow, L. F., Balu, S., Quake, S. R., Knowles, B. B., Burkholder, W. F., Solter, D. and Messerschmidt, D. M., 2013. Single-cell DNA-methylation analysis reveals epigenetic chimerism in preimplantation embryos. Science, 341(6150), pp. 1110-1112.

Guo, H., Zhu, P., Wu, X., Li, X., Wen, L. and Tang, F., 2013. Single-cell methylome landscapes of mouse embryonic stem cells and early embryos analyzed using reduced representation bisulfite sequencing. Genome research, 23(12), pp. 2126-2135.

Smallwood, S. A., Lee, H. J., Angermueller, C., Krueger, F., Saadeh, H., Peat, J., Andrews, S. R., Stegle, O., Reik, W. and Kelsey, G., 2014. Single-cell genome-wide bisulfite sequencing for assessing epigenetic heterogeneity. Nature methods, 11(8), pp. 817-820.

Picher, A. J., Budeus, B., Wafzig, O., Kruger, C., Garcia-Gomez, S., Martinez-Jimenez, M. I., Diaz-Talavera, A., Weber, D., Blanco, L. and Schneider, A., 2016. TruePrime is a novel method for whole-genome amplification from single cells based on TthPrimPol. Nature communications, 7: 13296

The invention claimed is:

1. A method for amplifying targeted methylated genomic DNA comprising:
   a) denaturing targeted methylated genomic DNA;
   b) incubating the targeted methylated genomic DNA with a polymerase and methyltransferase at a ratio of polymerase units to methyltransferase units between about 1:5 units and about 1:20 units under conditions to reproduce the targeted methylated genomic DNA and create amplified genomic methylated DNA molecules; and
   c) isolating the amplified genomic methylated DNA molecules.

2. The method of claim 1, wherein the ratio of polymerase units to methyltransferase units is about 1:15 units.

3. The method of claim 2, wherein the amount of targeted methylated genomic DNA that is incubated with the polymerase and methyltransferase is between about 5 picograms (pg) and about 1 microgram (μg).

4. The method of claim 3, wherein the amount of targeted genomic methylated DNA that is incubated with the polymerase and methyltransferase is between about 5 pg and about 10 pg.

5. The method of claim 2, wherein the targeted methylated genomic DNA is obtained from a tissue sample, a serum sample, a blood sample, a fecal sample, a urine sample, or a cheek or mouth swab.

6. The method of claim 2, wherein denaturing involves alkaline denaturation.

7. The method of claim 2, wherein the polymerase is a strand displacement polymerase.

8. The method of claim 2, wherein the methyltransferase is DNMT1.

9. The method of claim 2, wherein step b) further includes incubating the targeted methylated genomic DNA with an enzyme comprising a primase and a polymerase dual activity to synthesize primers during the conditions to reproduce the targeted methylated genomic DNA and create amplified genomic methylated DNA molecules.

10. The method of claim 2, further comprising preparing a separate master mix and an enzyme mix comprising the polymerase and methyltransferase prior to incubating in step b).

11. The method of claim 10, wherein the master mix includes an enzyme with a primase and a polymerase dual activity, dNTPs, buffer, and magnesium.

12. The method of claim 10, wherein the enzyme mix further comprises a methyl cofactor.

13. The method of claim 12, wherein the methyl cofactor is S-adenosyl methionine (SAM).

14. The method of claim 2, further comprising one or more of (1) treating the amplified genomic methylated DNA molecules with bisulfite, (2) sequencing the amplified genomic methylated DNA molecules, and (3) detecting or identifying 5-methylcytosine in the amplified genomic methylated DNA molecules.

15. The method of claim 2, further comprising denaturing the amplified genomic methylated DNA molecules.

16. The method of claim 15, further comprising enriching for denatured amplified genomic methylated DNA molecules.

17. The method of claim 16, wherein enriching for denatured amplified genomic methylated DNA molecules involves a 5mC antibody or a methyl-CpG binding protein.

18. The method of claim 16, wherein the method further comprises analyzing the enriched denatured amplified genomic methylated DNA molecules by quantitative PCR, sequencing, or an array-based analysis.

19. The method of claim 2, further comprising one or more of (1) amplifying and/or sequencing one or more target genomic regions using at least one pair of primers specific to the target genomic regions; (2) preparing a library from the amplified genomic methylated DNA molecules; (3) lysing one or more cells from a biological sample from a patient; and (4) extracting DNA from a biological sample from a patient.

20. The method of claim 2, wherein the ratio of polymerase units to methyltransferase units is about 1:10 units.

21. The method of claim 2, wherein the polymerase is Phi29 polymerase.

22. A method of analyzing methylated cell-free DNA from a cell-free biological sample from a patient comprising:
 a) denaturing methylated cell-free DNA (cfDNA) from the cell-free biological sample;
 b) incubating the methylated cfDNA with a polymerase and methyltransferase under conditions to reproduce the methylated cfDNA and create amplified methylated DNA molecules, wherein the polymerase and methyltransferase are present at a ratio between about 1:5 units to about 1:20 units; and,
 c) isolating the amplified methylated DNA molecules.

* * * * *

SEQUENCE LISTING

<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: NFATC1 forward primer

<400> SEQUENCE: 1 tttttgtaa taagaggaag tatagtttta                                    30

<210> SEQ ID NO 2
<211> LENGTH: 24
<212> TYPE: DNA
<213> ORGANISM: Artificial Sequence
<220> FEATURE:
<223> OTHER INFORMATION: NFATC1 reverse primer hypermethylated

<400> SEQUENCE: 2
atctcccaaa tccaaactac tatc                                         24

<210> SEQ ID NO 3
<211> LENGTH: 27
<212> TYPE: DNA
<213> ORGANISM: Artificial Sequence
<220> FEATURE:
<223> OTHER INFORMATION: MAPK8IP2 forward primer

<400> SEQUENCE: 3
ggttgtgtag tttttattga gtgttta                                27

<210> SEQ ID NO 4
<211> LENGTH: 21
<212> TYPE: DNA
<213> ORGANISM: Artificial Sequence
<220> FEATURE:
<223> OTHER INFORMATION: MAPK8IP2 reverse primer unmethylated

<400> SEQUENCE: 4 aatccccca aaaccctaa c                                        21

<210> SEQ ID NO 5
<211> LENGTH: 30
<212> TYPE: DNA
<213> ORGANISM: Artificial Sequence
<220> FEATURE:
<223> OTHER INFORMATION: FMR1 forward primer

<400> SEQUENCE: 5
gctcagctcc gtttcggttt cacttccggt                             30

<210> SEQ ID NO 6
<211> LENGTH: 22
<212> TYPE: DNA
<213> ORGANISM: Artificial Sequence
<220> FEATURE:
<223> OTHER INFORMATION: FMR1 reverse primer

<400> SEQUENCE: 6
cctccatctt ctcttcagcc ct                                     22

<210> SEQ ID NO 7
<211> LENGTH: 206
<212> TYPE: DNA
<213> ORGANISM: Artificial Sequence
<220> FEATURE:
<223> OTHER INFORMATION: NFATC1 locus: hypermethylated

<400> SEQUENCE: 7 cccttgcaa caagaggaag tacagcctca acggccggca gccgccctac tcaccccacc      60
actcgcccac gccgtccccg cacggctccc cgcgggtcag cgtgaccgac gactcgtggt    120
tgggcaacac cacccagtac accagctcgg ccatcgtggc cgccatcaac gcgctgacca    180
ccgacagcag cctggacctg ggagat                                         206

<210> SEQ ID NO 8
<211> LENGTH: 252
<212> TYPE: DNA
<213> ORGANISM: Artificial Sequence
<220> FEATURE:
<223> OTHER INFORMATION: MAPK8IP2 locus: unmethylated

<400> SEQUENCE: 8
ggctgtgcag tctctactga gtgctcaaag tccacttttta gccccagcca gcatcctctg     60
agtaccttgt gctcgattct gaatccagcc ctgctcggcg accctcgtgc agacgtcccc    120

```
gtgcagcccc ggtcagcacc ccgtggggac agctccgatc agcacccgac ggcggacagc        180
tcctcccgcg cctcccgcct cgcccgccac cccgctccgg gccgcacccg ggttagggtt        240
cctgggggga tc                                                            252

<210> SEQ ID NO 9
<211> LENGTH: 38
<212> TYPE: DNA
<213> ORGANISM: Artificial Sequence
<220> FEATURE:
<223> OTHER INFORMATION: NFATC1 locus WGA control group

<400> SEQUENCE: 9
tggttattgt ggttgttatt aatgtgttga ttattgat                                38

<210> SEQ ID NO 10
<211> LENGTH: 38
<212> TYPE: DNA
<213> ORGANISM: Artificial Sequence
<220> FEATURE:
<223> OTHER INFORMATION: NFATC1 locus 5mC-WGA group

<400> SEQUENCE: 10
cggttatcgt ggtcgttatt aacgcgttga ttatcgat                                38

<210> SEQ ID NO 11
<211> LENGTH: 33
<212> TYPE: DNA
<213> ORGANISM: Artificial Sequence
<220> FEATURE:
<223> OTHER INFORMATION: MAPK8IP2 locus WGA control group

<400> SEQUENCE: 11 tgattttgt gtagatgttt ttgtgtagtt ttg                                      33

<210> SEQ ID NO 12
<211> LENGTH: 33
<212> TYPE: DNA
<213> ORGANISM: Artificial Sequence
<220> FEATURE:
<223> OTHER INFORMATION: MAPK8IP2 locus 5mC-WGA group

<400> SEQUENCE: 12 tgattttgt gtagatgttt ttgtgtagtt ttg                                      33
```